(12) United States Patent
Vanella (10) Patent No.: US 9,757,736 B2
(45) Date of Patent: Sep. 12, 2017

(54) FILTRATION ASSEMBLY

(75) Inventor: Simone Vanella, Pesaro (IT)

(73) Assignee: TECNOLOGICA S.A.S. DI VANELLA SALVATORE & C., Pesaro (IT)

( * ) Notice: Subject to any disclaimer, the term of this patent is extended or adjusted under 35 U.S.C. 154(b) by 63 days.

(21) Appl. No.: 14/391,637

(22) PCT Filed: Apr. 13, 2012

(86) PCT No.: PCT/IT2012/000108
§ 371 (c)(1),
(2), (4) Date: Oct. 9, 2014

(87) PCT Pub. No.: WO2013/153563
PCT Pub. Date: Oct. 17, 2013

(65) Prior Publication Data
US 2015/0075379 A1 Mar. 19, 2015

(51) Int. Cl.
*B03C 3/41* (2006.01)
*B03C 3/47* (2006.01)
(Continued)

(52) U.S. Cl.
CPC *B03C 3/41* (2013.01); *A61L 9/20* (2013.01); *B03C 3/08* (2013.01); *B03C 3/12* (2013.01);
(Continued)

(58) Field of Classification Search
CPC combination set(s) only.
See application file for complete search history.

(56) References Cited

U.S. PATENT DOCUMENTS 4,227,446 A 10/1980 Sone et al.
4,496,375 A 1/1985 Le Vantine
(Continued)

FOREIGN PATENT DOCUMENTS

CN 2482752 Y 3/2002
CN 1364100 A 8/2002
(Continued)

OTHER PUBLICATIONS

Chinese Office Action, dated Jan. 14, 2016, Chinese Application No. 201280072364.X and pertinent English language translation (13 pages).
(Continued)

*Primary Examiner* — Duane Smith
*Assistant Examiner* — Sonji Turner
(74) *Attorney, Agent, or Firm* — Abelman, Frayne & Schwab (57) ABSTRACT

A filtration assembly (1), which comprises an enclosure (2) which defines inside it a duct (3) for the passage of a fluid which carries pollutant particles (A) to be removed. At a first transverse cross-section of the duct (3) at least one perforated conducting grille (4) is provided, which is kept at a negative electrical potential, so as to emit into the duct (3) electrons which can bond to the pollutant particles (A), consequently giving them a negative electrical charge. Inside the duct (3), downstream of the grille (4), at least one accumulation plate (5) is provided, kept at a positive electrical voltage, for collecting the pollutant particles (A) charged electrically negatively by the electrons emitted by the grille (4). Moreover, at least one deflection element (6) is arranged proximate to the accumulation plate (5) and is kept at a negative electrical potential in order to generate an electrical field inside the duct (3), with consequent redirection of the negatively electrically charged particles (A)
(Continued)

toward the accumulation plate (5). The assembly comprises at least one conducting filament (7), which faces and is proximate to a respective hole (8) of the grille (4). The filament (7) is kept at a negative electrical potential, for the emission of electrons, which can bond to the pollutant particles (A) carried at least by the portion of fluid that passes through the respective hole (8).

37 Claims, 6 Drawing Sheets (51) Int. Cl.
  *A61L 9/20* (2006.01)
  *B03C 3/08* (2006.01)
  *B03C 3/12* (2006.01)
  *B03C 3/36* (2006.01)

(52) U.S. Cl.
  CPC ............... *B03C 3/361* (2013.01); *B03C 3/47* (2013.01); *B03C 2201/04* (2013.01); *B03C 2201/10* (2013.01)

(56) References Cited

U.S. PATENT DOCUMENTS

| | | | |
|---|---|---|---|
| 5,492,557 A * | 2/1996 | Vanella | B03C 3/017 422/121 |
| 6,077,334 A * | 6/2000 | Joannou | B03C 3/155 96/66 |
| 6,635,106 B2 | 10/2003 | Katou et al. | |
| 7,101,424 B2 | 9/2006 | Wascher et al. | |
| 7,438,747 B2 * | 10/2008 | Luo | H01T 23/00 361/226 |
| 7,473,304 B2 * | 1/2009 | Besi | B01D 46/50 422/121 |
| 7,655,076 B2 * | 2/2010 | Griffiths | B03C 3/011 96/64 |
| 7,976,616 B2 * | 7/2011 | Alam | B03C 3/41 313/351 |
| 8,889,079 B2 * | 11/2014 | Zahedi | B01D 53/323 422/171 |
| 2007/0283810 A1 * | 12/2007 | Besi | B01D 46/50 96/64 |
| 2008/0190296 A1 | 8/2008 | Alam | |
| 2011/0126712 A1 | 6/2011 | Gefter | |
| 2011/0171094 A1 * | 7/2011 | Zahedi | B01D 53/323 423/245.1 |

FOREIGN PATENT DOCUMENTS

| | | | | |
|---|---|---|---|---|
| EP | 1864840 A1 | 12/2007 | | |
| IT | EP 0644379 A1 * | 3/1995 | ............. | B03C 3/155 |
| IT | WO 2005102535 A1 * | 11/2005 | ............. | B03C 3/08 |
| JP | 4027455 A | 1/1992 | | |
| JP | H08112549 A | 5/1996 | | |
| JP | 2004342542 A | 12/2004 | | |
| JP | 2009183807 A | 8/2009 | | |
| WO | 2004033104 A | 4/2004 | | |

OTHER PUBLICATIONS

Japanese Office Action, dated Jan. 26, 2016, Japanese Application No. 2015-505071 and pertinent English language translation (10 pages).

International Search Report from PCT/IT2012/000108 dated Nov. 22, 2012 (4 pages).

* cited by examiner

FILTRATION ASSEMBLY

RELATED APPLICATIONS

This application is a United States national phase application under 35 USC §371 of PCT/IT2012/000108 filed on Apr. 13, 2012, which is incorporated herein by reference in its entirety.

The present invention relates to a filtration assembly.

As is known, air introduced in enclosed spaces by means of climate-control, aeration, ventilation, heating systems et cetera is a potential carrier of pollutants of various kinds, among which organic pollutants, such as viruses, bacteria, spores, molds, fungi and the like, are highly dangerous (for people in the enclosed space).

For this purpose, filtration assemblies are sometimes installed at the air outlets directed toward the enclosed space and are intended indeed to remove selectively the pollutants according to their physical state (solid, gaseous, microbiological and electrical).

Therefore, according to known methods these filtration assemblies can have partitions made of fabric, designed to be struck by the stream of air before it is introduced in the enclosed space and capable of retaining the polluting particles and microorganisms that are present in the air.

These constructive solutions, however, are not free from drawbacks.

The retained pollutants in fact accumulate along the surface of the partition, progressively blocking its pores (reducing filtration efficiency) and therefore requiring periodic maintenance by specialized operators (accordingly with very high costs).

Moreover, the pollutants collected along the partition and not removed promptly from it can sometimes be reintroduced in the enclosed space the next time that the ventilation system is started.

These drawbacks are partially solved by the filtration assembly disclosed by the Applicant in the prior EPA 06425389.1 filed on 9 Jun. 2006.

The above mentioned application in fact discloses a device which comprises an outer enclosure which is provided with a perforated grille, to be arranged along the path of the air to be filtered, which has a preset negative electrical potential value and therefore is capable of emitting electrons when the fluid stream passes.

In greater detail, such perforated grille is provided with a plurality of pointed protrusions, adapted to scatter electrons when the fluid stream passes through the holes of the grille, in order to facilitate their bonding to the pollutant particles.

In this manner, the particles that carry the pollutants are charged electrically and can thus be attracted by a collecting plate with a positive electrical potential (provided with means for inactivating the microorganisms) arranged downstream of the grille.

However, this constructive solution, too, despite eliminating the need for frequent maintenance and the risk of reintroducing the pollutants in the enclosed space, is not free from drawbacks.

It has in fact been observed that the use of the device described above achieves absolutely unsatisfactory results (in terms of suppression of the pollutant particulate).

First of all, in fact, the amount of pollutants that is able to escape from the filter still remains rather high. Moreover, the filter described above proves itself totally ineffective against finer particles (with dimensions of less than 0.3 µm), which are instead the greatest health hazard for people.

The aim of the present invention is to solve the above mentioned problems, by providing an assembly that ensures high filtration effectiveness.

Within the scope of this aim, an object of the invention is to provide a filtration assembly that is highly effective also against ultra-fine particulate with dimensions on the order of nanometers.

A further object of the invention is to provide a filtration assembly that requires simple and infrequent maintenance.

Another object of the invention is to provide an assembly that ensures high reliability in operation.

Another object of the invention is to provide an assembly that can be obtained easily starting from commonly commercially available elements and materials.

Another object of the invention is to provide an assembly that has modest costs and is safe in application.

This aim and these objects are achieved by a filtration assembly, comprising an enclosure which defines inside it a duct for the passage of a fluid which carries pollutant particles to be removed, at a first transverse cross-section of said duct there being at least one perforated conducting grille, which is kept at a negative electrical potential, for the emission into said duct of electrons which can bond to the pollutant particles, consequently giving them a negative electrical charge, inside said duct, downstream of said grille, there being at least one accumulation plate, kept at a positive electrical voltage, for collecting the pollutant particles charged electrically negatively by the electrons emitted by said grille, at least one deflection element being arranged proximate to said accumulation plate and being kept at a negative electrical potential in order to generate an electrical field inside said duct, with consequent redirection of the negatively electrically charged particles toward said accumulation plate, characterized in that it comprises at least one conducting filament, which faces and is proximate to a respective hole of said grille, said filament being kept at a negative electrical potential, for the emission of electrons, which can bond to the pollutant particles carried at least by the portion of fluid that passes through said respective hole.

Further characteristics and advantages of the invention will become better apparent from the description of four preferred but not exclusive embodiments of the filtration assembly according to the invention, illustrated by way of non-limiting example in the accompanying drawings, wherein:

FIGS. 1 to 3 are views of the assembly according to the invention, in the first embodiment, more precisely:

FIGS. 4 to 6 are views of the assembly according to the invention in the second embodiment, more precisely:

FIGS. 7 and 8 are views of the assembly according to the invention in the third embodiment, more precisely;

FIGS. 9 and 10 are views of the assembly according to the invention in the fourth embodiment, more precisely:

With reference to the figures, the filtration assembly according to the invention, generally designated by the reference numeral 1, comprises an enclosure 2 which defines internally a passage duct 3 for a fluid, typically air, which carries pollutant particles A to be removed.

The assembly 1 can thus be arranged at a pipe of any climate control, aeration, ventilation, heating system and the like and can be preset for filtration and decontamination of the air that flows through the pipe before it is introduced in the enclosed space for which it is intended.

The enclosure 2 can thus be constituted by a tubular sleeve, which can be inserted coaxially along the pipe or can be defined by a portion of the pipe itself.

According to the preferred application, to which reference shall be made occasionally in the continuation of the present description, the enclosure 2 is instead a box-like body which can be installed at the outlet of systems such as for example the ones described above, thus forcing the air to pass through the duct 3 (which is internal to the box-like body) before it is finally introduced in the enclosed space toward which the outlet leads.

As mentioned earlier, the fluid that flows through the duct 3 is preferably air, but the use of the assembly 1 to filter different fluid types is not excluded and the possibility to use it in different fields of application, with respect to the ones described briefly in the preceding paragraphs, is provided without thereby abandoning the protective scope claimed herein.

The pollutant particles A to be removed can be of any type (both in terms of their electrical and/or microbiological properties and in terms of their physical solid, liquid or gaseous state, and can be organic or inorganic), but according to the preferred application, to which constant reference shall be made hereinafter, they are constituted by organic pollutants, such as viruses, bacteria, spores, molds, fungi and the like (or are inorganic substances which constitute a carrier for such pollutants).

As can be seen from the accompanying figures, at a first transverse cross-section of the duct 3 at least one perforated conducting grille 4 is provided, which is kept at a negative electrical potential (whose value can also be variable over time and can be chosen at will according to the specific requirements), so as to emit in the duct 3 electrons which can thus bond to the pollutant particles A carried by the fluid, which strikes and passes through the perforated grille 4, while it flows through the duct 3.

The pollutant particles A are thus given a negative electrical charge, which allows their collection by means of at least one accumulation plate 5, which is kept at a positive electrical potential and is arranged downstream of the grille 4, inside the duct 3.

The plate 5 can thus be removed easily periodically to clean it from the collected particles A, preventing excessive accumulations.

It is specified that it is possible to provide the assembly 1 with any number of accumulation plates 5, arranged in the duct 3 according to various configurations, according to the specific requirements: for example, the accompanying figures propose constructive solutions that resort to three accumulation plates 5 arranged in a parallel configuration along the duct 3.

Moreover, with further reference to the accompanying figures, the internal walls of the enclosure 2, at which two of the three accumulation plates 5 are arranged, can be covered with a covering film 2a made of insulating material (accordingly interposed between the walls and the plates 5).

In order to facilitate the collection of the negatively electrically charged particles A, at least one deflection element 6 is arranged proximate to the accumulation plate 5 (and preferably but not exclusively so as to face it) and is kept at a negative electrical potential (optionally of the same value as that of the grille 4), so as to generate an electrical field inside the duct 3, with consequent deflection of the particles A toward the accumulation plate 5.

The number of deflection elements 6 arranged inside the duct 3 also can be changed at will without abandoning the protective scope claimed herein. In the accompanying figures, in fact, along each duct 3 eight deflection elements 6 are provided, aligned in pairs along four mutually parallel rows (which are parallel to the internal walls of the enclosure 2 and to the accumulation plates 5, which they therefore face, in order to better deflect and precipitate the pollutant particles A and thus ensure an optimum result).

According to the invention, the filtration assembly 1 comprises at least one conducting filament 7, which faces and is proximate to a respective hole 8 of the grille 4. The filament 7 is kept at a negative electrical potential (which can also be equal to that of the grille 4 and/or of the deflection element 6), so as to constitute a privileged electron emission source, which is arranged exactly at the passage area of at least one portion of fluid (which indeed passes through the above cited respective hole 8), so as to ensure bonding to the pollutant particles A carried by the portion.

In particular, the filtration assembly 1 comprises at least one first conducting filament 7, which faces the respective hole 8, is proximate thereto and is arranged substantially downstream of the grille 4, and at least one second conducting filament 7, which faces the respective hole 8, is proximate thereto and is arranged substantially upstream of the grille 4.

Figure 1:
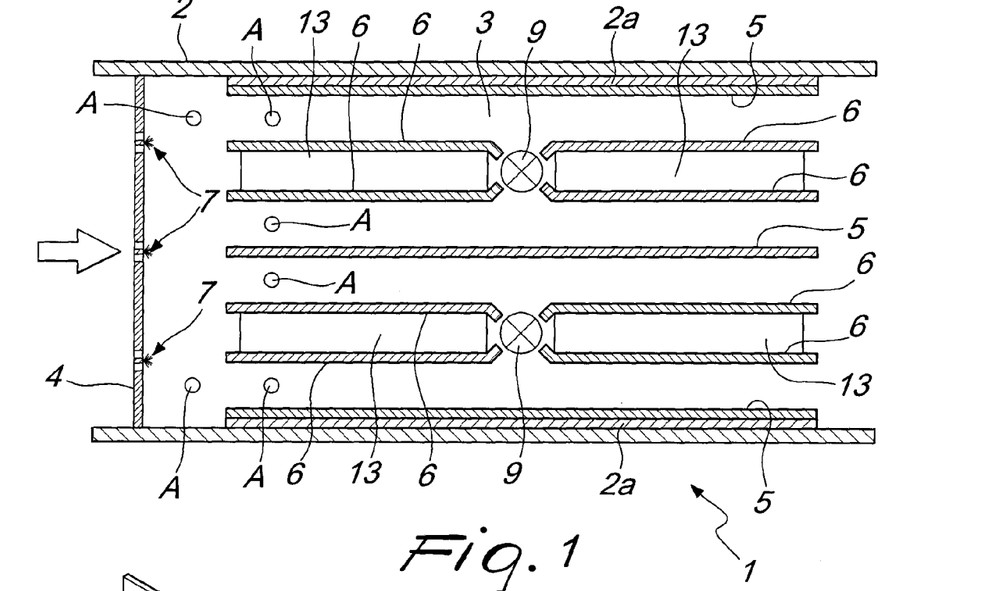
FIG. 1 is a schematic sectional side view of the assembly according to the invention, taken along an axial plane.
Figure 2:
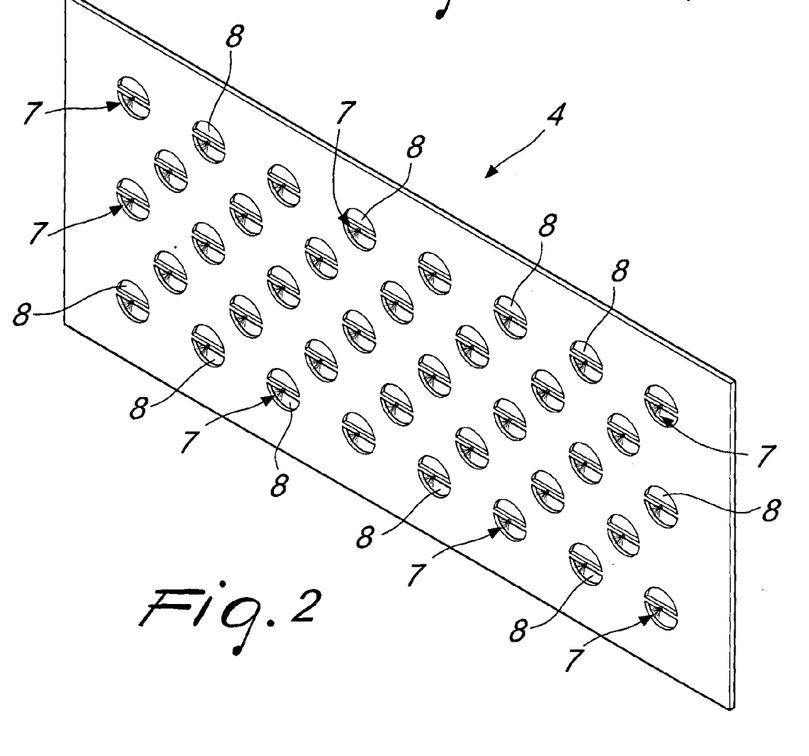
FIG. 2 is a perspective view of the conducting grille.
Figure 4:
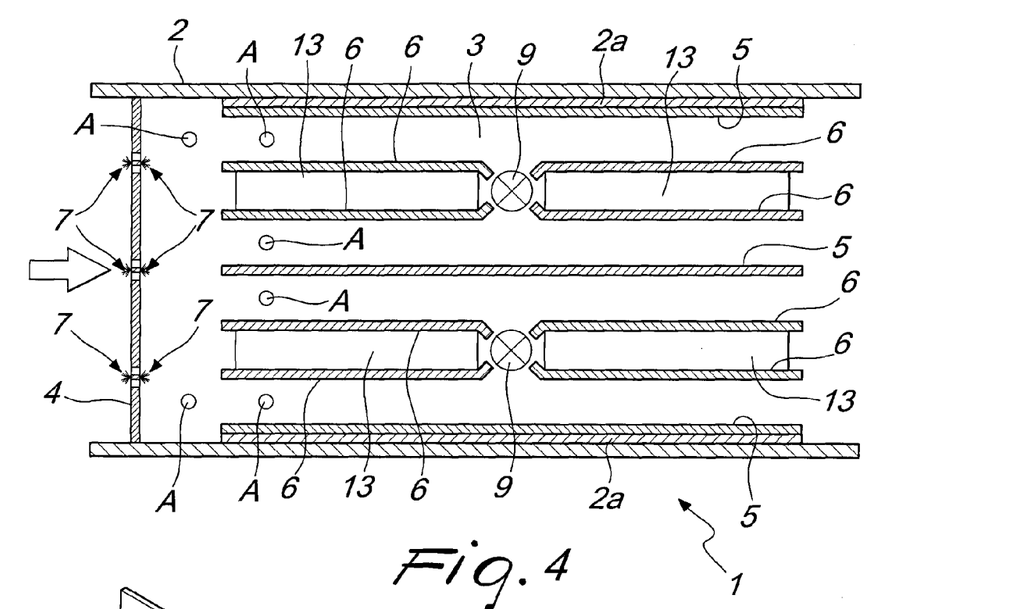
FIG. 4 is a schematic sectional side view of the assembly according to the invention, taken along an axial plane.
Figure 5:
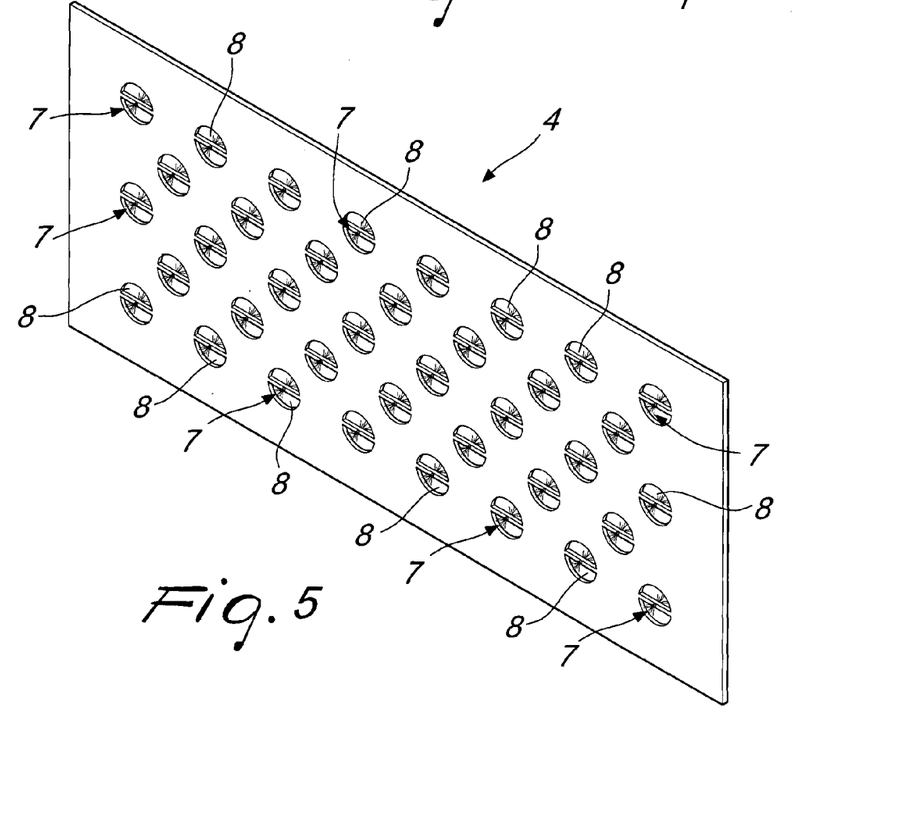
FIG. 5 is a perspective view of the conducting grille.

Therefore, constructive solutions in which at least one filament 7 is arranged only downstream (or only upstream) of the grille 4 (as in the example of FIGS. 1, 2 and 3), as well as (preferred) constructive solutions in which at least one filament 7 is arranged upstream of the grille 4 and at least one filament 7 is arranged downstream of it (as in the example of FIGS. 4, 5 and 6) are therefore within the protective scope claimed herein.

It is therefore useful to specify that in the continuation of the present description all the proposed constructive variations are understood to be conceived (even where this is not indicated specifically) both with filaments 7 arranged only downstream (or only upstream) of the grille 4, and with filaments 7 arranged both upstream and downstream of the grille 4 (a solution which ensures the highest filtration effectiveness).

In particular, the assembly 1 comprises a plurality of filaments 7 (a number chosen at will without thereby abandoning the protective scope claimed herein), which face and are proximate to at least one respective hole 8 of the grille 4. Each filament 7 is kept at a predefined negative electrical potential, so as to emit electrons, which can bond to the pollutant particles A carried by the fluid that passes at least through the respective hole 8.

Even more precisely, each hole 8 of the grille 4 faces and is proximate to a plurality of filaments 7, which are kept at a predefined negative electrical potential.

In this manner, the emission of the electrons by the grille 4 is concentrated at the filaments 7, and since the filaments 7 face the holes 8 through which the entire mass of fluid is forced to pass, the assembly 1 according to the invention ensures a very high effectiveness, since the fluid current passes through the region in which the emission of electrons is the highest, thus ensuring the bonding thereof to a very large number of pollutant particles A.

Conveniently, each filament 7 has a different length and is chosen preferably (but not exclusively) of the multipolar type and made of metallic material.

Figure 3:
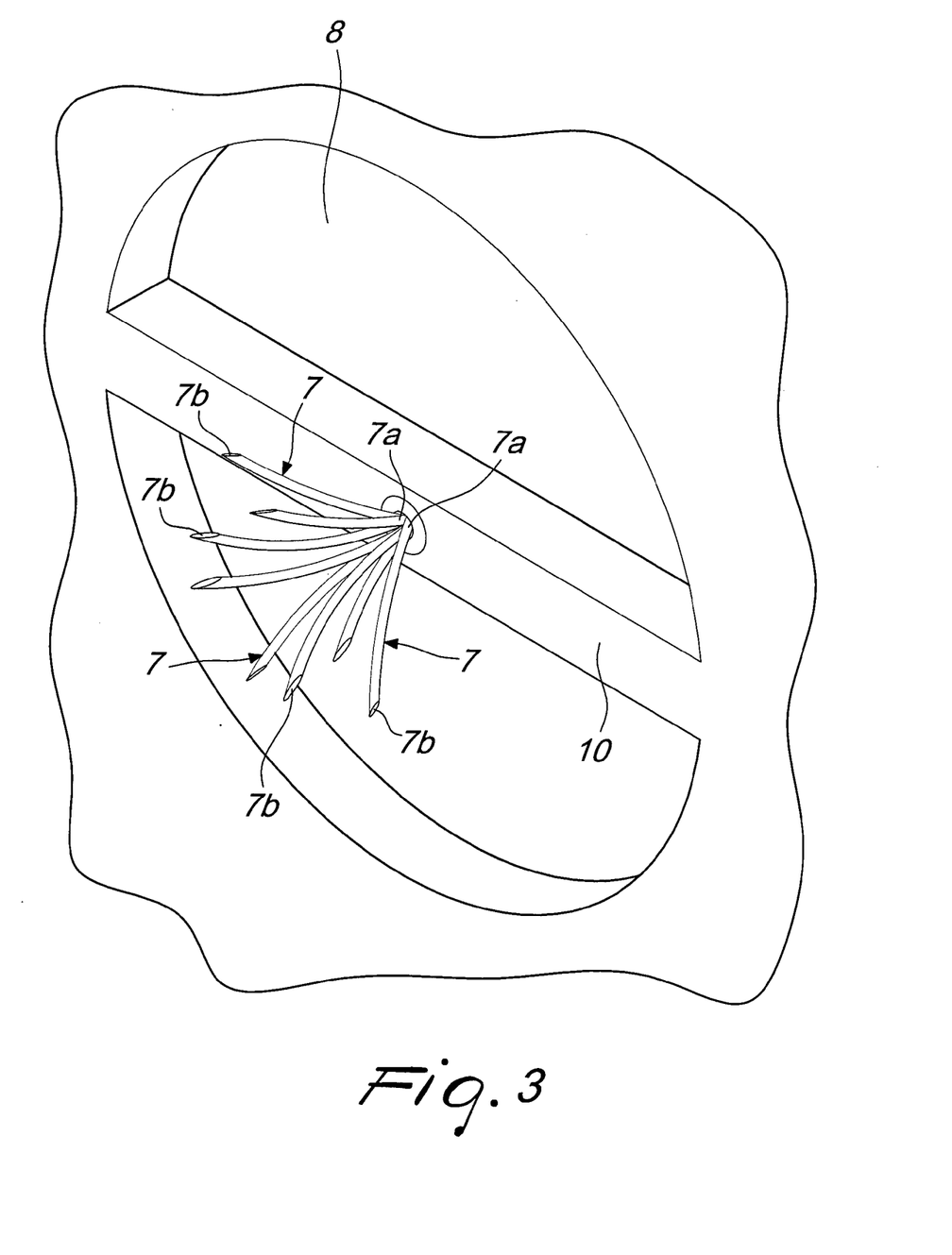
FIG. 3 is a highly enlarged-scale view of a detail of FIG. 2.
Figure 6:
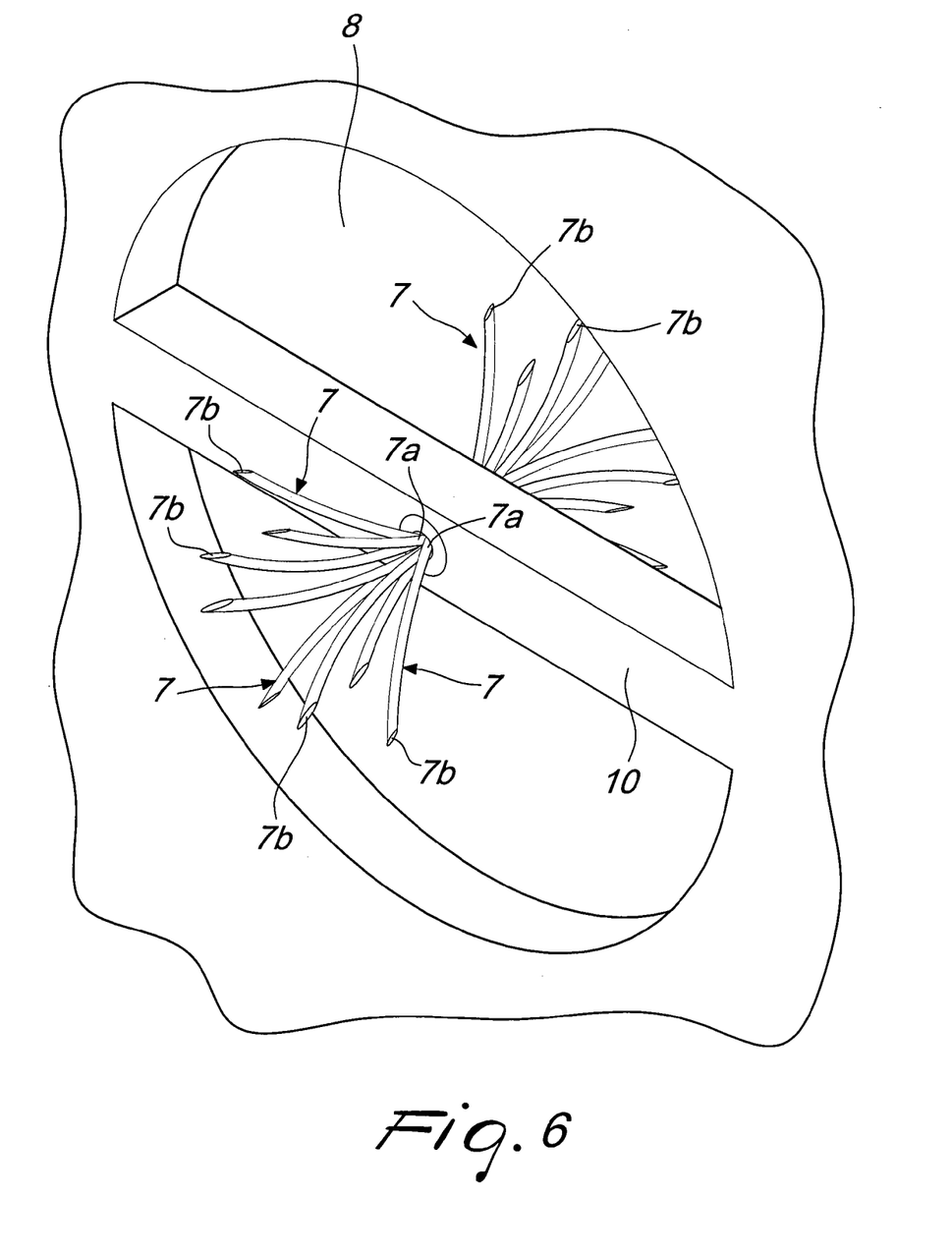
FIG. 6 is a highly enlarged-scale view of a detail of FIG. 5.

According to the preferred constructive solution, cited by way of non-limiting example of the application of the invention, each filament 7 is coupled, at a first fixed end 7a thereof, to the grille 4. As shown in FIGS. 3 and 6, at the opposite end each filament 7 has a second free end 7b, which is wedge-shaped so as to define a substantially pointed configuration (which tapers outward) with a consequent further increase in the emission of electrons.

Conveniently, the filtration assembly 1 comprises at least one unit 9 for inactivating organic pollutants, such as viruses, bacteria, spores, molds, fungi and the like, contained in the pollutant particles A carried by the fluid. The unit 9 faces and is proximate to the accumulation plate 5, so as to render harmless the pollutants. Moreover, it is specified that it is possible to arrange along the duct 3 a number at will of units 9 (for example two, as in the accompanying figures).

Even if one does not wish to remove periodically the accumulation plate 5, the presence of the unit 9 ensures that the organic pollutant particles A collected on the plate 5 cannot proliferate and are instead rendered fully harmless. Therefore, any separation thereof from the plate 5, with consequent potential introduction in the downstream enclosed space, is not a source of biological contamination and of harm to people.

In particular, according to a possible constructive solution, the inactivation unit 9 is constituted substantially by a UV ray germicidal lamp, which faces and is proximate to the accumulation plate 5, for its continuous irradiation, with consequent inactivation of any type of microorganism, regardless of the inactivation time.

According to a constructive solution of considerable practical interest, proposed by way of non-limiting example of the application of the invention, each hole 8 is substantially circular and is crossed by a diametrical rib 10. The first ends 7a of all the filaments 7 that face and are proximate to a same respective hole 8 are coupled stably substantially to the center of the rib 10, as shown for example in FIGS. 3 and 6.

Conveniently, the assembly 1 according to the invention comprises at least one reference frame, which is arranged proximate to the holes 8 and kept at a different electrical potential, with respect to the electrical potential of the filaments 7, and is preferably kept at an electrical potential which is equal to the ground potential. In this manner, inside the duct 3, and more precisely between the plate 5 and the frame, it is possible to generate a flow of electrons, emitted by the filaments 7 and attracted indeed by the frame, which is oriented along a predefined direction.

Figure 7:
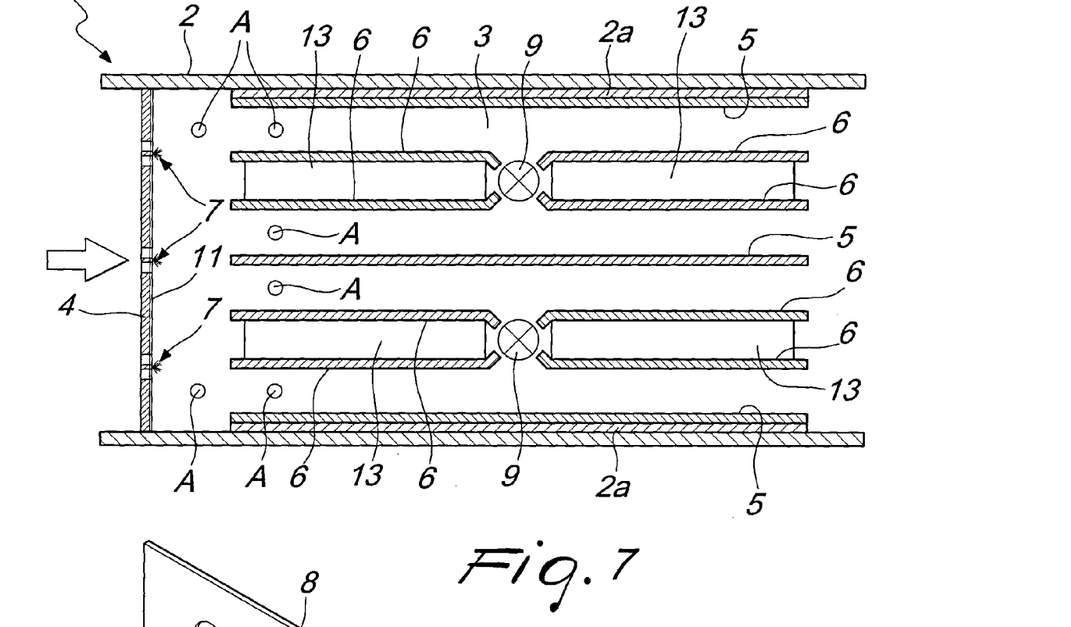
FIG. 7 is a schematic sectional side view of the assembly according to the invention, taken along an axial plane.
Figure 8:
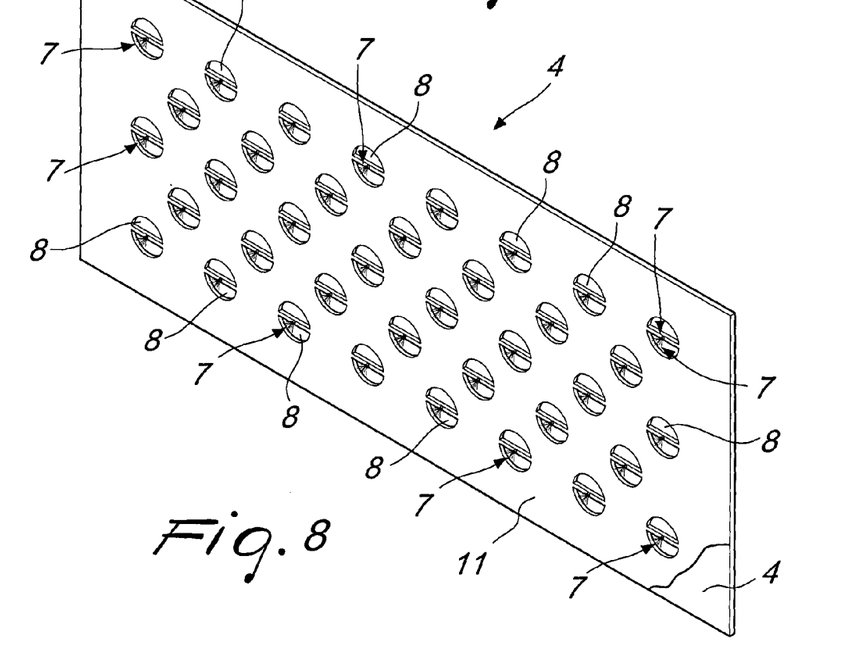
FIG. 8 is a perspective view of the conducting grille.

According to a possible embodiment, proposed in FIGS. 7 and 8 by way of non-limiting example of the application of the invention, the frame, kept at an electrical potential that is preferably equal to the ground potential, is constituted substantially by a covering sheet 11 made of metallic material (for example copper) arranged at least along the face of the grille 4 that is directed toward the accumulation plate 5 (so as to cover it partially or, according to the preferred solution, completely).

In this manner, the electrons emitted by the filaments 7 and attracted by the sheet 11 are given a trajectory that has at least one (initial) portion that is substantially perpendicular to the direction of advancement of the fluid, since they are released by the free ends 7b of the filaments 7, and fall substantially onto the plane defined by the grille 4, on which the sheet 11 indeed lies.

However, the possibility is not excluded to arrange a respective sheet 11 on each face of the grille 4 if the filaments 7 are arranged both downstream and upstream of the grille 4 (as described in the preceding pages).

According to a different embodiment, the frame, kept as already noted at an electrical potential that is preferably equal to the ground potential, is constituted substantially by a metallic mesh, which is arranged parallel to the grille 4 and in its vicinity to attract the electrons emitted by the filaments 7.

If the filaments 7 are arranged only downstream or only upstream of the grille 4, the metal mesh correspondingly can be arranged only downstream or only upstream of the grille 4. If instead the filaments are arranged both downstream and upstream of the grille 4, assemblies 1 are used which are provided with a single metallic mesh or two which are conveniently arranged upstream and downstream of the grille 4.

Figure 9:
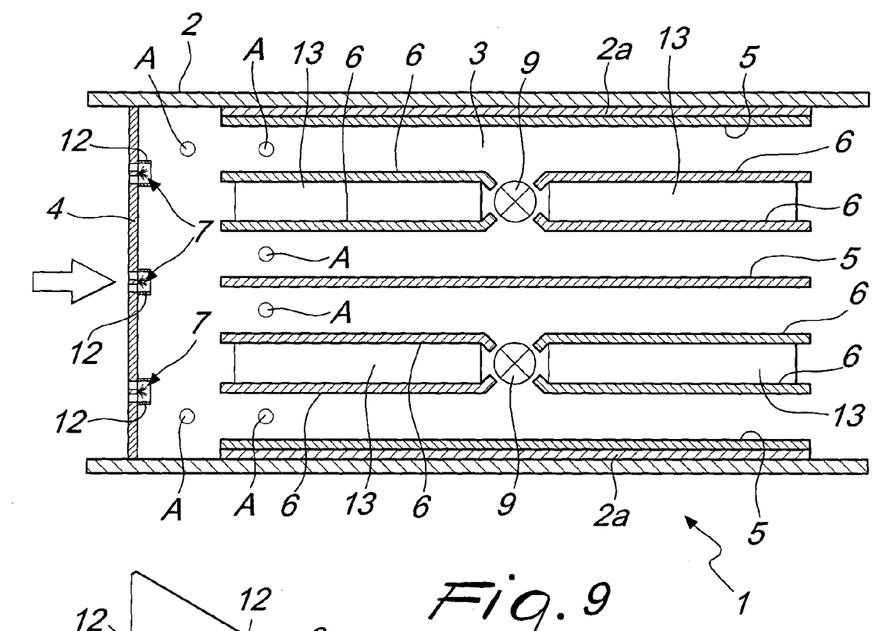
FIG. 9 is a schematic sectional side view of the assembly according to the invention, taken along an axial plane.
Figure 10:
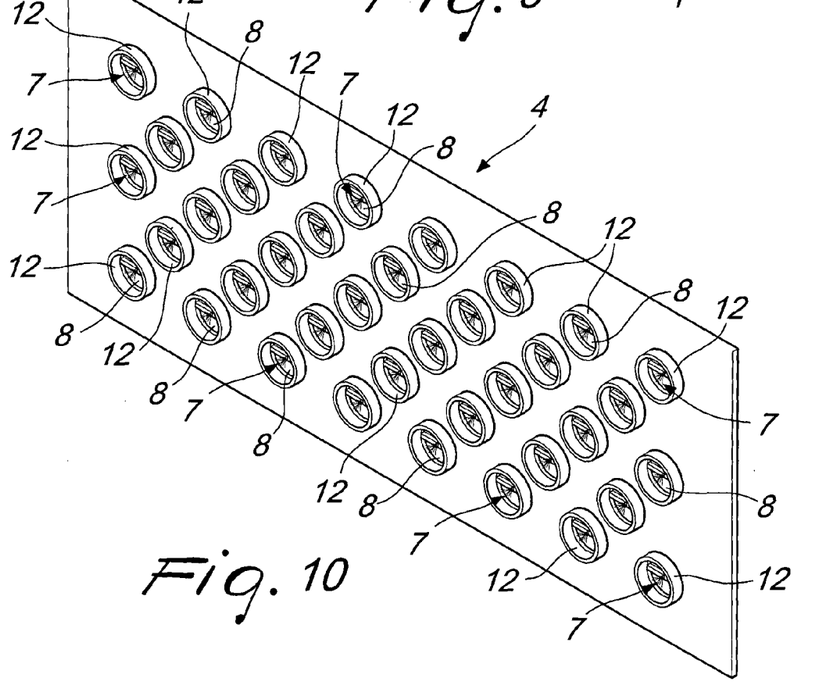
FIG. 10 is a perspective view of the conducting grille.

According to a further embodiment, illustrated by way of non-limiting example in FIGS. 9 and 10, each substantially circular hole 8 is provided with a circumferential lip 12, which has a substantially cylindrical shape and extends from the rim of the holes 8, at right angles to the grille 4, and can be directed toward the accumulation plate 5 and/or in the opposite direction (depending on the arrangement of the filaments 7). In this embodiment, the frame, kept at an electrical potential that is preferably equal to the ground potential, is constituted by a covering layer (made of metallic material, preferably copper) of the top of each lip 12, sized appropriately to extend axially beyond the free ends 7b of the filaments 7.

In this manner, the electrons emitted by the filaments 7 (and especially by the free ends 7b thereof) and attracted by the lips 12 are made to follow a trajectory that has at least one (initial) portion which is substantially parallel to the fluid advancement direction, ensuring that the flow of electrons has a portion of trajectory that substantially coincides with the fluid stream, extending the period of time for which the electrons and the pollutant particles A carried by the air can make contact, facilitating their bonding.

According to a further possible embodiment, the holes 8 have a substantially hexagonal shape (but assemblies 1 provided with differently shaped holes 8 might also be provided): a substantially triangular tab protrudes from each side of the hexagonal perimeter of the holes 8 (so as to define, for the grille 4, the appearance of a grater) and is directed toward the accumulation plate 5 and/or away from it.

A reference frame then faces the holes 8 and is kept at a different electrical potential, with respect to the electrical potential of the filaments 7, and preferably kept at an electrical potential that is equal to the ground potential, to generate a flow of electrons, emitted by the filaments 7 and by the tabs, and attracted by the frame, which is oriented along a predefined direction. In this embodiment, the frame can be constituted preferably by a metallic grid-like framework, which is arranged in a parallel configuration downstream of the grille 4 (and/or upstream thereof) and in its vicinity.

Moreover, it is specified that it is possible to provide the assembly 1 with an ionizer, located substantially at an end section of the duct 3, therefore at the outlet of the air from the assembly 1, adapted to rebalance the negative electrical charges that are present in the air.

Furthermore, as can be seen from the accompanying figures, the assembly 1 according to the invention can comprise means 13 for supporting and shaping the deflection elements 6.

Operation of the assembly according to the invention is as follows.

The assembly 1, as already noted, can be installed along a tube or at the outlet of systems and equipments for ventilation, climate control and the like, of any enclosed space (civil, hospital and the like), also of any means of transport (aircraft, trains, ships, military vehicles, spacecraft and others) in order to protect the health of people. In the medical and hospital field, the assembly 1 can furthermore be used also to isolate individual beds in case of epidemics.

In any case, whatever the intended application (included or not among the ones briefly described above), the air (or other fluid) to be filtered passes through the duct 3 (substantially comprised between the accumulation plates 5 and the deflection elements 6) and defined inside the enclosure 2.

In greater detail, the entire mass of air passes through the holes 8 of the grille 4 and then strikes the filaments 7, which scatter electrons (since the grille 4 and the filaments 7 are kept at a negative electrical potential). The electrons (optionally directed conveniently toward the reference frame, which is preferably kept at ground potential) can thus bond to the pollutant particles A, giving them a negative electrical charge.

The accumulation plates 5 are then arranged appropriately downstream of the grille 4 and, by being kept at a positive electrical potential, attract the electrically negatively charged pollutant particles A, thus removing them from the air.

In order to facilitate this result, proximate to the accumulation plates 5 the deflection elements 6 are provided, which help to create an electrical field that facilitates the collection of the pollutant particles A on the plates 5.

The choice to resort to filaments 7 arranged at the holes 8 crossed by the fluid current ensures maximum filtration efficiency, producing a high scattering of the electrons and concentrating it in the region that surrounds the free ends 7b of the filaments 7 (which is indeed crossed by the fluid current), thus ensuring the coupling between a very large number of electrons and pollutant particles A (and therefore their consequent collection downstream on the plates 5).

Indeed the high filtration efficiency, achieved by means of the constructive choices described above, also makes it possible to remove from the fluid stream even ultra-fine particulate and therefore even pollutant particles A of particularly small size (often the most dangerous for people), such as pollutant particles with a size of less than 0.3 μm and down to dimensions on the order of nanometers.

Moreover, the presence of the germicidal lamp (or other inactivation unit 9) makes it possible to render harmless, by eliminating them, the organic pollutants (furthermore avoiding their proliferation), allowing maintenance interventions with a limited frequency, even just once a year, for example.

A contribution to this result is also given by the choice to entrust filtration to a substantially electrical effect and not to the mechanical properties of a porous membrane, as occurs when using conventional filters: the latter is in fact subject, in case of poor maintenance, to progressive blocking of the pores, with consequent reduction of filtering effectiveness. Vice versa, the capacity to charge negatively the pollutant particles A and to collect them on the accumulation plates 5 is not affected by the frequency with which cleaning and maintenance is performed thereon.

Moreover, it should be noted that the assembly 1 opposes no appreciable resistance to the passage of air and therefore upon starting it does not release material of any kind into the enclosed space, since the pollutant particles A are retained on the plates 5. Again, this result allows infrequent (and very simple) maintenance interventions without thereby compromising filtration effectiveness (which remains maximum even without performing any maintenance and/or entrusting it to unspecialized workers).

In practice it has been found that the assembly according to the invention fully achieves the intended aim, since the presence of at least one conducting filament, kept at a negative electrical potential, which faces and is proximate to a respective hole of the grille, facilitates the bonding of the electrons emitted by the filament to at least the portion of the fluid to be filtered, which passes through the hole, ensuring a high filtration effectiveness for the assembly.

The invention thus conceived is susceptible of numerous modifications and variations, all of which are within the scope of the appended claims. All the details may furthermore be replaced with other technically equivalent elements.

For example, the possibility is not excluded to provide assemblies 1 constituted by a plurality of modules arranged in series along a pipe or at the outlet of a system, in which each module has the elements described in the preceding pages and therefore at least one grille 4, at least one accumulation plate 5 and at least one deflection element 6.

In this manner it is possible to increase further the overall effectiveness of the assembly 1 according to the invention, while keeping limited the speed at which the air passes through the duct 3 (another factor which enables to ensure maximum filtration).

In the examples of embodiment shown, individual characteristics, given in relation to specific examples, may actually be interchanged with other different characteristics that exist in other examples of embodiment.

In practice, the materials used, as well as the dimensions, may be any according to requirements and to the state of the art.

Where technical features mentioned in any claim are followed by reference signs, those reference signs have been included for the sole purpose of increasing the intelligibility of the claims and accordingly such reference signs do not have any limiting effect on the interpretation of each element identified by way of example by such reference signs.

The invention claimed is:

1. A filtration assembly, comprising an enclosure which defines inside it a duct for the passage of a fluid which carries pollutant particles to be removed, at a first transverse cross-section of said duct at least one perforated conducting grille, said grille comprising a plurality of holes, said grille being kept at a negative electrical potential, for emission into said duct of electrons which can bond to the pollutant particles, consequently giving them a negative electrical charge, inside said duct, downstream of said grille, at least one accumulation plate being provided, kept at a positive electrical voltage, for collecting the pollutant particles charged electrically negatively by the electrons emitted by said grille, at least one deflection element being arranged proximate to said accumulation plate and being kept at a negative electrical potential in order to generate an electrical field inside said duct, with consequent redirection of the negatively electrically charged particles toward said accumulation plate, wherein at least one conducting filament, which faces and is proximate to a respective hole of said grille, said filament being kept at a negative electrical potential, for the emission of electrons, which can bond to the pollutant particles carried at least by the portion of fluid that passes through said respective hole, wherein at least one first conducting filament, which faces and is proximate to said respective hole and is arranged substantially downstream of said grille and at least one second conducting filament, which faces and is proximate to said respective hole and is arranged substantially upstream of said grille.

2. The filtration assembly according to claim 1, wherein it comprises a plurality of said filaments, which face and are proximate to at least one respective hole of said grille, each one of said filaments being kept at a predefined negative electrical potential in order to emit electrons that can bond to the pollutant particles carried by the fluid that passes through at least said respective hole.

3. The filtration assembly according to claim 1, wherein a plurality of said filaments, kept at a predefined negative electrical potential, faces and is proximate to each one of said holes of said grille.

4. The filtration assembly according to claim 1, wherein each one of said filaments has a different length, said filaments being chosen of a multipolar type and being made of metallic material.

5. The filtration assembly according to claim 1, wherein each one of said filaments is coupled, at a first fixed end, to said grille, at the opposite end each one of said filaments having a second free end, which is wedge-shaped, to define a shape which is substantially pointed, with a consequent increase in the emission of electrons.

6. The filtration assembly according to claim 1, wherein it comprises at least one inactivation unit for inactivating organic pollutants such as viruses, bacteria, spores, molds, fungi and the like, contained in the pollutant particles carried by the fluid, said unit facing and being proximate to said at least one accumulation plate.

7. The filtration assembly according to claim 6, wherein said at least one inactivation unit is constituted substantially by a UV ray germicidal lamp, which faces and is proximate to said at least one accumulation plate, for its constant irradiation, with consequent inactivation of the biological pollutants.

8. The filtration assembly according to claim 1, wherein each one of said holes is substantially circular, each one of said holes being crossed by a diametrical rib, said first ends of each one of said filaments, which face and are proximate to a same respective hole, being coupled stably substantially to the center of said rib.

9. The filtration assembly according to claim 1, wherein it comprises at least one reference frame, which is arranged proximate to said holes and is kept at a different electrical potential with respect to the electrical potential of said filaments, and is kept at an electrical potential which is equal to ground potential, in order to generate a flow of electrons, emitted by said filaments and attracted by said frame, which is oriented along a predefined direction.

10. The filtration assembly according to claim 9, wherein said frame, kept at an electrical potential equal to ground potential, is substantially constituted by a covering sheet made of metallic material, which is arranged at least along the face of said grille that is directed toward said at least one accumulation plate, in order to impart to the electrons emitted by said filaments and attracted by said sheet paths that have at least one portion that is substantially perpendicular to the direction of advancement of the fluid.

11. The filtration assembly according to claim 9, wherein said frame, kept at an electrical potential equal to the ground potential, is constituted substantially by a metallic mesh, which is arranged parallel to said grille, and in its vicinity, to attract the electrons emitted by said filaments.

12. The filtration assembly according to claim 9, wherein each one of said holes are substantially circular and have a circumferential lip, which is substantially cylindrical and protrudes from the rim of said holes at right angles to said grille, said frame, kept at an electrical potential equal to the ground potential, being constituted by a layer for covering the top of each one of said lips, in order to impart to the electrons emitted by said filaments and attracted by said lips trajectories that have at least one portion which is substantially parallel to the fluid advancement direction.

13. The filtration assembly according to claim 1, wherein each one of said holes is substantially hexagonal, a substantially triangular appendage protruding from each side of the hexagonal perimeter of said holes, which face a reference frame, kept at a different electrical potential with respect to the electrical potential of said filaments, and kept at an electrical potential equal to ground potential, for the generation of a flow of electrons emitted by said filaments and by said tabs and attracted by said frame, which is oriented along a predefined direction, said frame being constituted by a metallic lattice-like mesh which is arranged parallel to said grille, and in its vicinity.

14. A filtration assembly, comprising an enclosure which defines inside it a duct for the passage of a fluid which carries pollutant particles to be removed, at a first transverse cross-section of said duct at least one perforated conducting grille being provided, said grille comprising a plurality of holes, said grille being kept at a negative electrical potential, for emission into said duct of electrons which can bond to the pollutant particles, consequently giving them a negative electrical charge, inside said duct, downstream of said grille, at least one accumulation plate being provided, kept at a positive electrical voltage, for collecting the pollutant particles charged electrically negatively by the electrons emitted by said grille, at least one deflection element being arranged proximate to said accumulation plate and being kept at a negative electrical potential in order to generate an electrical field inside said duct, with consequent redirection of the negatively electrically charged particles toward said accumulation plate, wherein at least one conducting filament, which faces and is proximate to a respective hole of said grille, said filament being kept at a negative electrical potential, for the emission of electrons, which can bond to the pollutant particles carried at least by the portion of fluid that passes through said respective hole, wherein said respective hole is substantially circular and crossed by a diametrical rib, a first end of said filament, which faces and are proximate to said respective hole, being coupled stably substantially to the center of said rib.

15. The filtration assembly according to claim 14, wherein it comprises a plurality of said filaments, which face and are proximate to at least one respective hole of said grille, each one of said filaments being kept at a predefined negative electrical potential in order to emit electrons that can bond to the pollutant particles carried by the fluid that passes through at least said respective hole, each one of said holes is substantially circular and crossed by a diametrical rib, first ends of each one of said filament, which face and are proximate to a same respective hole, being coupled stably substantially to the center of said rib.

16. The filtration assembly according to claim 14, wherein a plurality of said filaments, kept at a predefined negative electrical potential, faces and is proximate to each one of said holes of said grille, each one of said holes is substantially circular and crossed by a diametrical rib, first ends of each one of said filament, which face and are proximate to a same respective hole, being coupled stably substantially to the center of said rib.

17. The filtration assembly according to claim 16, wherein each one of said filaments has a different length, said filaments being chosen of a multipolar type and being made of metallic material.

18. The filtration assembly according to claim 16, wherein each one of said filaments is coupled, at a first fixed end, to said grille, at the opposite end each one of said filaments having a second free end, which is wedge-shaped, to define a shape which is substantially pointed, with a consequent increase in the emission of electrons.

19. The filtration assembly according to claim 14, wherein it comprises at least one inactivation unit for inactivating organic pollutants such as viruses, bacteria, spores, molds, fungi and the like, contained in the pollutant particles carried by the fluid, said unit facing and being proximate to said at least one accumulation plate.

20. The filtration assembly according to claim 19, wherein said at least one inactivation unit is constituted substantially by a UV ray germicidal lamp, which faces and is proximate to said at least one accumulation plate, for its constant irradiation, with consequent inactivation of the biological pollutants.

21. The filtration assembly according to claim 15, wherein it comprises at least one reference frame, which is arranged proximate to said holes and is kept at a different electrical potential with respect to the electrical potential of said filaments, and is kept at an electrical potential which is equal to ground potential, in order to generate a flow of electrons, emitted by said filaments and attracted by said frame, which is oriented along a predefined direction.

22. The filtration assembly according to claim 21, wherein said frame, kept at an electrical potential equal to ground potential, is substantially constituted by a covering sheet made of metallic material, which is arranged at least along the face of said grille that is directed toward said at least one accumulation plate, in order to impart to the electrons emitted by said filaments and attracted by said sheet paths that have at least one portion that is substantially perpendicular to the direction of advancement of the fluid.

23. The filtration assembly according to claim 21, wherein said frame, kept at an electrical potential equal to the ground potential, is constituted substantially by a metallic mesh, which is arranged parallel to said grille, and in its vicinity, to attract the electrons emitted by said filaments.

24. The filtration assembly according to claim 21, wherein each one of said substantially circular holes has a circumferential lip, which is substantially cylindrical and protrudes from the rim of said holes at right angles to said grille, said frame, kept at an electrical potential equal to the ground potential, being constituted by a layer for covering the top of each one of said lips, in order to impart to the electrons emitted by said filaments and attracted by said lips trajectories that have at least one portion which is substantially parallel to the fluid advancement direction.

25. A filtration assembly, comprising an enclosure which defines inside it a duct for the passage of a fluid which carries pollutant particles to be removed, at a first transverse cross-section of said duct at least one perforated conducting grille, said grille comprising a plurality of holes, said grille being kept which is kept at a negative electrical potential, for emission into said duct of electrons which can bond to the pollutant particles, consequently giving them a negative electrical charge, inside said duct, downstream of said grille, at least one accumulation plate being provided, kept at a positive electrical voltage, for collecting the pollutant particles charged electrically negatively by the electrons emitted by said grille, at least one deflection element being arranged proximate to said accumulation plate and being kept at a negative electrical potential in order to generate an electrical field inside said duct, with consequent redirection of the negatively electrically charged particles toward said accumulation plate, wherein at least one conducting filament, which faces and is proximate to a respective hole of said grille, said filament being kept at a negative electrical potential, for the emission of electrons, which can bond to the pollutant particles carried at least by the portion of fluid that passes through said respective hole, wherein it comprises at least one reference frame, which is arranged proximate at least to said respective hole and is kept at a different electrical potential with respect to the electrical potential of said filament, and is kept at an electrical potential which is equal to ground potential, in order to generate a flow of electrons, emitted by said filament and attracted by said frame, which is oriented along a predefined direction.

26. The filtration assembly according to claim 25, wherein it comprises a plurality of said filaments, which face and are proximate to at least one respective hole of said grille, each one of said filaments being kept at a predefined negative electrical potential in order to emit electrons that can bond to the pollutant particles carried by the fluid that passes through at least said respective hole.

27. The filtration assembly according to claim 25, wherein a plurality of said filaments, kept at a predefined negative electrical potential, faces and is proximate to each one of said holes of said grille.

28. The filtration assembly according to claim 27, wherein each one of said filaments has a different length, said filaments being chosen of a multipolar type and being made of metallic material.

29. The filtration assembly according to claim 27, wherein each one of said filaments is coupled, at a first fixed end, to said grille, at the opposite end each one of said filaments having a second free end, which is wedge-shaped, to define a shape which is substantially pointed, with a consequent increase in the emission of electrons.

30. The filtration assembly according to claim 25, wherein it comprises at least one inactivation unit for inactivating organic pollutants such as viruses, bacteria, spores, molds, fungi and the like, contained in the pollutant particles carried by the fluid, said unit facing and being proximate to said at least one accumulation plate.

31. The filtration assembly according to claim 30, wherein said at least one inactivation unit is constituted substantially by a UV ray germicidal lamp, which faces and is proximate to said at least one accumulation plate, for its constant irradiation, with consequent inactivation of the biological pollutants.

32. The filtration assembly according to claim 27, wherein each one of said holes is substantially circular, each one of said holes being crossed by a diametrical rib, said first ends of each one of said filaments, which face and are proximate to a same respective hole, being coupled stably substantially to the center of said rib.

33. The filtration assembly according to claim 25, wherein said frame, kept at an electrical potential equal to ground potential, is substantially constituted by a covering sheet made of metallic material, which is arranged at least along the face of said grille that is directed toward said at least one accumulation plate, in order to impart to the electrons emitted by said filament and attracted by said sheet paths that have at least one portion that is substantially perpendicular to the direction of advancement of the fluid.

34. The filtration assembly according to claim 25, wherein said frame, kept at an electrical potential equal to the ground potential, is constituted substantially by a metallic mesh, which is arranged parallel to said grille, and in its vicinity, to attract the electrons emitted by said filament.

35. The filtration assembly according to claim 25, wherein at least said respective hole is substantially circular and has a circumferential lip, which is substantially cylindrical and protrudes from the rim of said holes at right angles to said grille, said frame, kept at an electrical potential equal to the ground potential, being constituted by a layer for covering the top of each one of said lips, in order to impart to the electrons emitted by said filament and attracted by said lips trajectories that have at least one portion which is substantially parallel to the fluid advancement direction.

36. The filtration assembly according to claim 25, wherein at least said respective hole is substantially hexagonal, a substantially triangular appendage protruding from each side of the hexagonal perimeter of said hole, which face a reference frame, kept at a different electrical potential with respect to the electrical potential of said filament, and kept at an electrical potential equal to ground potential, for the generation of a flow of electrons emitted by said filament and by said tabs and attracted by said frame, which is oriented along a predefined direction, said frame being constituted by a metallic lattice-like mesh which is arranged parallel to said grille, and in its vicinity.

37. A filtration assembly, comprising an enclosure which defines inside it a duct or the passage of a fluid which carries pollutant particles to be removed, at a first transverse cross-section of said duct at least one perforated conducting grille, said grille comprising a plurality of holes, said grille being kept at a negative electrical potential, for emission into said duct of electrons which can bond to the pollutant particles, consequently giving them a negative electrical charge, inside said duct, downstream of said grille, at least one accumulation plate being provided, kept at a positive electrical voltage, for collecting the pollutant particles charged electrically negatively by the electrons emitted by said grille, at least one deflection element being arranged proximate to said accumulation plate and being kept at a negative electrical potential in order to generate an electrical field inside said duct, with consequent redirection of the negatively electrically charged particles toward said accumulation plate, wherein at least one conducting filament, which faces and is proximate to a respective hole of said grille, said filament being kept at a negative electrical potential, for the emission of electrons, which can bond to the pollutant particles carried at least by the portion of fluid that passes through said respective hole, wherein at least said respective hole is substantially hexagonal, a substantially triangular appendage protruding from each side of the hexagonal perimeter of said respective hole, which faces a reference frame, kept at a different electrical potential with respect to the electrical potential of said filament, and kept at an electrical potential equal to ground potential, for the generation of a flow of electrons emitted by said filament and by said tabs and attracted by said frame, which is oriented along a predefined direction, said frame being constituted by a metallic lattice-like mesh which is arranged parallel to said grille, and in its vicinity.

* * * * *